United States Patent [19]

Schneider et al.

[11] 4,242,529

[45] Dec. 30, 1980

[54] HYDROGENOLYSIS OF 2,5-NORBORNADIENE SATURATED ENDO-ENDO HEXACYCLIC DIMER

[75] Inventors: Abraham Schneider, Overbrook Hills; Harry K. Myers, Jr., Aston, both of Pa.

[73] Assignee: Sun Oil Company of Pennsylvania, Philadelphia, Pa.

[21] Appl. No.: 942,860

[22] Filed: Sep. 15, 1978

[51] Int. Cl.$^2$ .............................................. C09C 13/28
[52] U.S. Cl. ................................... 585/353; 585/360; 585/14; 149/1
[58] Field of Search ................. 260/666 PY; 585/360, 585/353

[56] References Cited

PUBLICATIONS

M. Naseem Akhtar et al., J. Chem. Soc. Perkin II pp. 1412–1414, 1976.
Thomas J. Katz et al., Chem. Ab. 70:87128q, 1969.
Nancy Acton et al., J. Amer. Chem. Soc. 94:15, 5446–5456, 1972.
Thomas J. Katz et al., Tetrahedron Letters, No. 27, pp. 2601–2605, 1967.
M. N. Akhtar et al., J. Amer. Chem. Soc. 96:1 pp. 276–277, 1974.
H. A. Quinn et al., J. of Catalysis 26, 333–337, 1972.
M. N. Akhtar et al., J. Chem. Soc. Chem. Comm. pp. 155–156, 1974.

*Primary Examiner*—Veronica O'Keefe
*Attorney, Agent, or Firm*—J. Edward Hess; Donald R. Johnson; Anthony Potts, Jr.

[57] ABSTRACT

Hydrogenolysis of a saturated endo-endo dihydronorbornadiene hexacyclic dimer involves the use of a catalytic amount of a Group VIII metal and the presence of hydrogen. The resulting pentacyclic isomers can be used as a diluent for depressing the freezing point of the saturated hexacyclic dimer which is a component of a high density missile fuel.

9 Claims, No Drawings

HYDROGENOLYSIS OF 2,5-NORBORNADIENE SATURATED ENDO-ENDO HEXACYCLIC DIMER

BACKGROUND OF THE INVENTION

The invention herein described was made in the course of or under a contract thereunder with the United States Air Force Systems Command.

This invention relates to the hydrogenolysis of a saturated endo-endo dimer of norbornadiene, hereinafter referred to as HNN. Particularly the invention relates to the preparation of an isomeric pentacyclic liquid mixture from HNN.

The aforementioned isomeric liquid mixture can be used as a high energy missile fuel in either jet or rocket propulsion or as a diluent for other similar mixtures. Jet propulsion includes a jet engine which can be used for a missile, an aircraft and others and includes the three basic types, i.e. ramjet, turbojet and pulse jet. The term rocket generally refers to a device containing fuel incorporating its own oxygen or oxidizing agent.

Norbornadiene (bicyclo-(2.2.1)-2,5-heptadiene) can be prepared by reacting cyclopentadiene and acetylene at an elevated temperature, see U.S. Pat. No. 2,875,256 (Cl 260-666). Norbornadiene has the following structure:

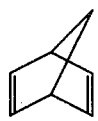

It can be dimerized into an olefinic endo-endo homo dimer having the following structure:

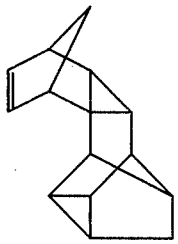

I

Dimerization of norbornadiene to compound I is disclosed in "The Stereochemical Course of Metal Catalyzed Cycloaddition Reactions of Norbornadiene", T. J. Katz et al., Tetrahedron Letters, No. 27, pp 2601-2605, 1967. The dimerization involves the use of a group VIII metal complex. Compound I is also disclosed in Chemical Abstracts, 91:1, Jan. 1, 1969, page 265, 87128q. The dimerization is also disclosed in "Dimerization and Trimerization of Norbornadiene by Soluble Rhodium Catalysts," Nancy Acton et al., Journal of the American Chemical Society, 94:15, July 26, 1972.

The olefinic bond in compound I can be hydrogenated. Generally a hydrogenation catalyst such as 5% rhodium-on-alumina is satisfactory. The temperature and pressure used for hydrogenation can be mild, e.g. about 125° C. and 100 psig of hydrogen.

Hydrogenolysis of 3,3-dimethylnortricyclene and nortricyclene-3-spirocyclopropane using rhodium or platinum catalysts supported on pumice and palladium on silica is reported in J. C. S. Perkin II, 1976, pages 1412-1414, "Reactions over Metal Catalysts. Part II, Hydrogenolysis of 3,3-Dimethylnortricyclene and Nortricyclene-3-spirocyclopropane", M. N. Akhtar et al. Also use of transition metals, e.g. palladium for isomerization of cyclic hydrocarbons such as endo-endo-2,3-trimethylene is disclosed in Journal of Catalysts 26, 333-337, 1972, "Skeletal Rearrangement of Some Cyclic Hydrocarbons Catalyzed by Palladium," H. A. Quinn et al. Use of platinum or palladium with various supports in hydrogenolysis of certain cyclopropyl rings is reported in Journal of the American Chemical Society, 96:1, Jan. 9, 1974, "Hydrogenolysis of Substituted Nortricyclenes over Supported Metal Catalyst, Methyl Migrations and Skeletal Rearrangements," M. N. Akhtar et al. In addition, use of supported platinum or palladium is compared with the use of platinum in acetic acid in the hydrogenolysis of certain nortricyclenes in J.C.S. Chem. Comm, 1974, pages 155-156, "Unusual Alkyl Group Directing Effects During Cyclopropane Ring Hydrogenolysis," M. N. Akhtar et al.

SUMMARY OF THE INVENTION

Hydrogenolysis of HNN occurs when using a catalytic amount of one of the Group VIII metals in the presence of hydrogen. The foregoing metal can be supported by carbon, alumina, and other known supports. The resulting HNN pentacyclic isomeric mixture when blended with HNN lowers the freezing point thereby enhancing the HNN's use as a high density missile fuel.

DESCRIPTION

The hydrogenolysis of HNN to pentacyclic isomers via present invention can be represented by the following formula reaction:

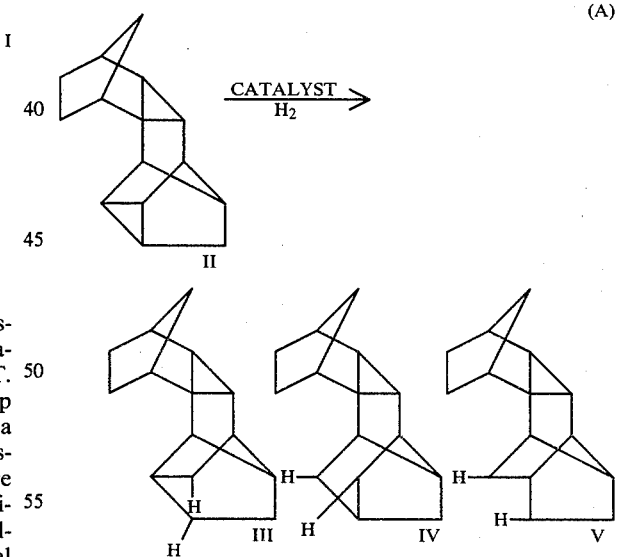

(A)

Compounds III, IV and V are pentacyclic isomers of each other. As can be seen the cyclopropane ring has been opened differently thereby forming different isomers. In effect isomers III, IV and V are formed from Compound II by breaking open the cyclopropane ring of HNN. During the reaction some of Compound II may be modified to other forms, not shown.

The catalyst can be anyone of the Group VIII metals which can be supported by carbon, alumina, kieselguhr, silica alumina and/or other known supports. While the metal can be present by itself, generally it is supported by an inert supporter to provide a more uniform distribution and a larger surface area of the active metal. When the metal is supported the concentration of the metal present is in the range between from about 0.1 wt.% to about 10 wt.% of the total catalyst. The metals of Group VIII are iron, cobalt, nickel, ruthenium, rhodium, palladium, osmium, iridium and platinum with palladium, nickel, rhodium and platinum preferred.

The catalyst is used in a catalytic amount. While a very small amount or a very large amount, relative to the amount of the hydrocarbon feed, of the catalyst can be used, commercial considerations favor a more limited range. Depending upon such variables as HNN feed rate, reactor size, kind of system, temperature, and mixing, if any, a more practical amount of catalyst to the amount of HNN is about 0.5 wt.% to about 15 wt.%.

Hydrogen needs to be present during reaction (A). The pressure of the hydrogen can vary substantially, however, generally economics favor using as low a hydrogen pressure as is possible and yet one which is satisfactory as to rate and product quality. While a pressure range between from about atmospheric to about 5000 psig is usable a preferred pressure range is between from about 25 to about 1000 psig.

The temperature of reaction A can vary, however, economics can favor using a lower temperature while a faster reaction rate is favored by a higher temperature. A high temperature which causes decomposition of the hydrocarbon feed or product or causes coking on the catalyst is to be avoided. While a temperature range between from about 50° C. to about 350° C. could be used a preferred temperature range is between from about 75° C. to about 300° C.

While the HNN feed can contain other similar hydrocarbons, such hydrocarbons should not adversely affect the activity of the catalyst. Further, the similar hydrocarbons should not adversely influence the desired resulting properties of the treated mixture. Thus for optimum results, the feed can consist essentially of HNN which itself can be a mixture of isomers but preferably it is essentially compound II.

After the hydrogenolysis, i.e. the opening of the cyclopropane ring, the catalyst can be separated by various known means from the hydrocarbon product. The hydrocarbon product itself can be separated from any unreacted feed if desired or the pentacyclic isomers can be separated from any other product formed. Need for the separation of the hydrocarbons in the product depends on the specifications set for the missile fuel.

The following Examples illustrate the invention along with a comparative run.

EXAMPLES

Accompanying Table summarizes the data obtained from the examples (Runs 1-8) which illustrate the invention. Shown in the Table are the catalysts used, the temperature and hydrogen pressure and the amount of isomers, i.e. III, IV and V, which was determined by vapor phase chromatography (vpc) analysis. Other structures may have been formed but these were not identified.

TABLE

Hydrogenolysis of Saturated Endo-Endo Hexacyclic Dimer of Norbornadiene

| Run No. | Catalyst Used[a] | Temp. °C.[c] | $H_2$ Pressure, psig[c] | Time[b] | Wt. % in VPC Sample[e] Pentacyclic Isomers[d] | Remaining HNN[e] |
|---|---|---|---|---|---|---|
| 1 | 5% Pd/alumina | 100-200 | 100 | 288 | 63 | 0 |
| 2 | 10% Pd/C | 200 | 100 | 160 | 55 | 13 |
| 3 | 60% Ni/Kieselguhr | 244 | 83-107 | 420 | 17 | 65 |
| 4 | 60% Ni/Kieselguhr | 179 | 99-135 | 402 | 17 | 58 |
| 5 | 64% Ni/Silica Alumina | 157 | 100 | 186 | 11 | 73 |
| 6 | 5% Rh/alumina | 210 | 100 | 438 | 53 | 35 |
| 7 | 5% Rh/alumina (4 wt. %) | 179 | 115 | 3000 | 78 | 0 |
| 8 | 5% Ru/alumina | 193 | 137 | 220 | 7.5 | 88 (est) |

Notes
[a] Amount of catalyst used was 10 wt.% except as shown.
[b] Minutes
[c] Temperature shown is generally maximum temperature; pressure is generally maximum pressure.
[d] Pentacyclics refers to structures III, IV and V shown in reaction A.
[e] Other products were not identified.

The general procedure used to obtain the data in the Table was as follows. HNN (purity 94.1%) along with the named catalyst were charged to a stirred or rocking stainless steel autoclave. The autoclave was charged with hydrogen to produce the pressure shown at the desired temperature and then heated with the maximum temperature reached as shown. The hydrogen absorption (as indicated by the change in pressure) indicated breakage of the cyclopropane carbon-carbon bonds. After the reaction appeared to be complete, the contents and the autoclave were allowed to cool and the hydrocarbon product filtered to remove the catalyst. The filtered hydrocarbon was then analyzed via vpc.

Use of Group VIII metals and supports other than those mentioned in the Table will yield analogous results.

We claim:
1. Process for the liquid phase hydrogenolysis of a saturated endo-endo dihydronorbornadiene hexacyclic dimer comprising:
   (a) contacting a dimer having the following structure,

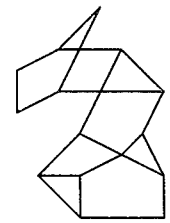

with a catalytic amount of a Group VIII metal and in the presence of hydrogen;
   (b) having the contacting occur, in the absence of a solvent, at a temperature in the range between from about 50° C. to about 350° C.; and (c) continuing the contacting until the cyclopropane ring of the dimer is opened.

2. Process according to claim 1 wherein the amount of catalyst to the dimer is in the range between from about 0.5 wt.% to about 15 wt.%.

3. Process according to claim 1 wherein the metal is selected from the group consisting of palladium, nickel, rhodium and platinum.

4. Process according to claim 1 wherein the temperature is in the range between from about 75° C. to about 300° C.

5. Process according to claim 1 wherein the pressure of the hydrogen is in the range between from about atmospheric to about 1000 psig.

6. Process according to claim 5 wherein the amount of catalyst to the dimer is in the range between from about 0.5 wt.% to about 15 wt.% and the temperature is in the range beween from about 75° C. to about 300° C.

7. Process according to claim 6 wherein the metal is selected from the group consisting of palladium, nickel, rhodium and platinum.

8. Process according to claim 7 wherein the pressure of the hydrogen is in the range between from about 25 psig to about 1000 psig.

9. Process according to claim 8 wherein the concentration of the metal present on the catalyst is in the range between from about 0.1 wt.% to about 10 wt.%.

* * * * *